United States Patent
Huang et al.

(10) Patent No.: US 8,244,334 B2
(45) Date of Patent: Aug. 14, 2012

(54) METHODS AND SYSTEMS FOR BLOOD FLOW MEASUREMENT USING DOPPLER OPTICAL COHERENCE TOMOGRAPHY

(75) Inventors: David Huang, South Pasadena, CA (US); Yimin Wang, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 1158 days.

(21) Appl. No.: 12/101,006

(22) Filed: Apr. 10, 2008

(65) Prior Publication Data

US 2009/0005691 A1 Jan. 1, 2009

Related U.S. Application Data

(60) Provisional application No. 60/910,871, filed on Apr. 10, 2007, provisional application No. 60/975,114, filed on Sep. 25, 2007, provisional application No. 61/035,871, filed on Mar. 12, 2008.

(51) Int. Cl.
*A61B 6/00* (2006.01)
(52) U.S. Cl. ......................................... 600/476
(58) Field of Classification Search .................... 600/476
See application file for complete search history.

(56) References Cited

U.S. PATENT DOCUMENTS

| | | | |
|---|---|---|---|
| 5,830,147 A | 11/1998 | Feke et al. | |
| 6,665,456 B2 * | 12/2003 | Dave et al. | 385/11 |
| 6,944,551 B2 * | 9/2005 | Chen et al. | 702/49 |
| 7,359,062 B2 * | 4/2008 | Chen et al. | 356/479 |
| 2004/0088123 A1 | 5/2004 | Ji | |
| 2006/0187462 A1 | 8/2006 | Srinivasan et al. | |

OTHER PUBLICATIONS

Pederson et al. "Measurement of absolute flow velocity vector using dual-angle, delay-encoded Doppler optical coherence tomography" Optics Letters, vol. 32, No. 5, Mar. 2007, pp. 506-508.
White et al. "In vivo dynamic human retinal blood flow imaging using ultra-high-speed spectral domain optical Doppler tomography" Optical Express, vol. 11, No. 25, Dec. 2003, pp. 3490-3497.
Yang et al. "High speed, wide velocity dynamic range Doppler optical coherence tomography (Part I): System design, signal processing, and performance" Optical Express, vol. 11, No. 7, Apr. 2003, pp. 794-809.
International Search Report for corresponding PCT application PCT/US08/59954 lists the references above.

* cited by examiner

*Primary Examiner* — Jacqueline Cheng
(74) *Attorney, Agent, or Firm* — DLA Piper LLP (US)

(57) ABSTRACT

This invention provides methods for non-invasive, real-time measuring and/or monitoring of local blood flow in a subject. Methods of the invention generally include the steps of obtaining Doppler shift images of at least two planes intersecting blood vessels at the scanned location; determining Doppler angles using the Doppler shift images; and then using the Doppler angles thus determined together with the Doppler shift signals to arrive at a measure of the volumetric blood flow. Also provided are systems and software for performing the methods.

30 Claims, 11 Drawing Sheets

US 8,244,334 B2

METHODS AND SYSTEMS FOR BLOOD FLOW MEASUREMENT USING DOPPLER OPTICAL COHERENCE TOMOGRAPHY

CROSS-REFERENCE TO RELATED APPLICATIONS

This application claims priority to the following U.S. provisional applications: Provisional Application No. 60/910,871, filed Apr. 10, 2007, entitled "METHOD FOR TOTAL RETINAL BLOOD FLOW MEASUREMENT"; Provisional Application No. 60/975,114, filed Sep. 25, 2007, entitled "TOTAL RETINAL BLOOD FLOW MEASUREMENT BY CIRCUMPAPILLARY FOURIER DOMAIN DOPPLER OPTICAL COHERENCE TOMOGRAPHY"; and Provisional Application No. 61/035,871, file Mar. 12, 2008, entitled "METHOD FOR TOTAL RETINAL BLOOD FLOW MEASUREMENT". The benefit under 35 USC §119 (e) of the United States provisional application is hereby claimed. The above priority applications are hereby incorporated herein by reference.

STATEMENT OF FEDERALLY SPONSORED RESEARCH AND DEVELOPMENT

The present invention is made, at least in part, with the support of grants from National Institute of Health (NIH grants R01 EY013516 and P30 EY03040). The government has certain rights in the invention.

FIELD OF THE INVENTION

The invention pertains to the field of optical coherence tomography. More particularly, the invention pertains to methods and systems for measuring blood flow in the retina and other body parts using Doppler optical coherence tomography.

BACKGROUND OF THE INVENTION

Tools capable of providing accurate, non-invasive, and quantitative structural and blood flow measurement of body parts in vivo are highly desirable in applications such as medical diagnosis and therapeutic progress monitoring. In this respect, optical coherence tomography (OCT) has been seen as a promising technology for providing such a capability.

Optical coherence tomography [1] is a recently developed technology that is capable of providing high-resolution cross-sectional imaging and is commonly used in the diagnosis and management of retinal diseases [2-4] and glaucoma [5, 6]. In addition to obtaining morphological images, OCT can also detect a Doppler shift of reflected light, which provides information on flow and movement [7-9]. Several investigators have studied the visualization of blood flow and flow dynamics using Doppler OCT [10-14]. The availability of Fourier Domain OCT allows the measurement of the Doppler shift, but this information alone only correlates to the blood flow in the direction of the scanning beam. Blood movement in the direction perpendicular to the scanning beam is not directly reflected in the Doppler shift. Thus, in order to measure volumetric flow, one must also know the incident angle between the scanning beam and the direction of the blood flow. This information cannot be obtained from a single cross-sectional OCT image, hence, volumetric flow measurement by Doppler OCT was hitherto not possible.

Therefore, there still exists a need for methods and tools that can overcome the problems in the art to provide practical, efficient, fast, sensitive, non-invasive and accurate measurements of in vivo blood flow.

SUMMARY OF THE INVENTION

Accordingly, one object of the present invention is to provide a optical tomography based method for measuring and/or monitoring blood flow in a non-invasive manner that can be performed in real-time.

A further object of the present invention is to provide systems and devices capable of non-invasively measuring blood flow in a subject by optical coherence tomography in real-time.

These and other objects of the present invention, which will become more apparent in conjunction with the following detailed description of the preferred embodiments, either along or in combinations thereof, have been satisfied by the invention of a method of performing and analyzing Doppler Fourier optical coherence tomography scans that is capable of decoupling the Doppler angles from the Doppler shift data obtained in the scans.

More specifically, in one aspect, the present invention provides a method for measuring in vivo blood flow in a predefined region of a subject using Doppler optical coherence tomography. Methods according to embodiments of the present invention generally include the steps of: (1) scanning the region with a scanning pattern that has at least two planes in which the planes cross blood vessels within the region; (2) analyzing the obtained OCT data to determine Doppler shifts and angles between each of the blood vessels and the incident scanning beam; and (3) determining a volumetric blood flow rate using the Doppler shift and incident angles of the beam (i.e., the Doppler angle).

The scanning patterns are preferably concentric circles, parallel lines, or arcs. Other scanning patterns may also be used so long as the patterns have a regular geometry that can yield two Doppler scan images, allowing a formulation of an equation to calculate the Doppler angles for each of the blood vessels.

In another aspect, the present invention also provides methods and systems for measuring and/or monitoring local blood flow in a subject that is indicative of a diseased condition by utilizing the Doppler Fourier optical coherence tomography based methods of blood flow measurement in accordance with embodiments of the present invention.

Also provided are computer systems and computer readable medium for performing methods of the present invention.

Other aspects and advantages of the invention will be apparent from the following description and the appended claims.

DETAILED DESCRIPTION

Figure 1:
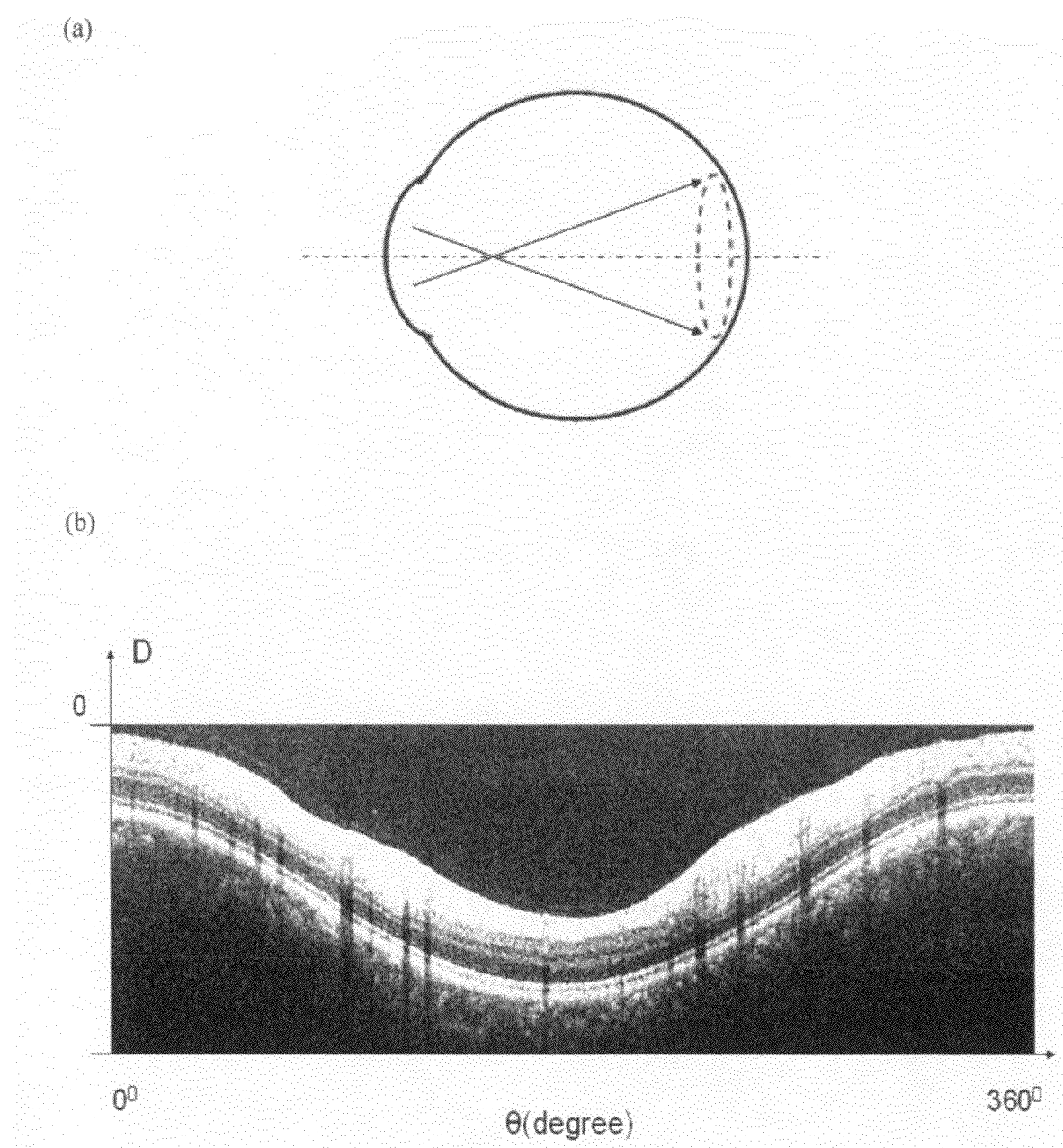
FIG. 1 shows exemplary OCT scans in accordance with embodiments of the present invention. (a) A circular retinal OCT scan is performed with a beam that rotates in a cone pattern. The apex of the cone is the nodal point of the eye. (b) The cylindrical OCT image is unfolded to fit a rectangular display where the horizontal axis corresponds to scanning angle from 0 to 360 degrees and the vertical axis corresponds to the depth dimension along the axis of beam propagation.

In order to facilitate a full and complete understanding of the present invention, the following theoretical discussion is provided. However, it will be appreciated by those skilled in the art that the invention is not bound by any particular theoretical or mathematical formulation. The following discussion is provided for the sole purpose of illustration only and other formulations of the concept disclosed herein are also possible and are within the skill of the art given benefit of the present disclosure.

Theory

In Doppler OCT, light reflected by moving blood incurs a Doppler frequency shift (Δf) proportional to the flow velocity component parallel to the axis of the probe beam. If the angle between the probe beam and the direction of blood flow is known, the Doppler shift may be simplified to $$\Delta f = -2nV \cos \alpha / \lambda_0 \quad (1)$$

where n is the refractive index of the medium, V is the total flow velocity, α is the angle between the OCT beam and the flow, V cos α is the parallel velocity component, and $\lambda_0$ is the center wavelength of the light. In FD-OCT [13, 14, 16, 17], this frequency shift Δf introduces a phase shift ΔΦ in the spectral interference pattern that is captured by the line camera. With fast Fourier transform (FFT), the phase difference between sequential axial scans at each pixel is calculated to determine the Doppler shift.

One limitation of a phase resolved flow measurement is an aliasing phenomenon caused by the 2π ambiguity in the arctangent function. This phenomenon limits the maximum determinable Doppler shift to $\Delta f = 1/(2\tau)$, where τ is the time difference between sequential axial lines. Thus, the maximum detectable speed is $V = \lambda_0/(4n\tau \cos \alpha)$. The minimum detectable flow velocity is determined by the phase noise of the FD-OCT system. In this scheme, knowledge of the relative angle α between the probe beam and flow direction is required in order to determine the real flow speed (refer to equation 1).

To resolve the above mentioned problem, the inventors have devised a strategy for determining the relative angle by utilizing scans of multiple planes. To illustrate the strategy of the present invention, an exemplary derivation based on a double circular scanning pattern (DCSP) is used. Again, it will be appreciated by one of ordinary skill in the art that other scanning patterns may also be suitably used to implement the strategy of the present invention.

Referring first to FIG. 1a, there is shown a diagrammatic representation of an OCT sampling beam scanning a circular pattern on the retina. In the circular scan, the probe beam moves on a cone during scanning. The apex of the cone is the nodal point in the eye. FIG. 1b is an exemplary OCT image that shows the retina structure crossed by the scanning cone. In FIG. 1b, the lateral axis represents the angular distribution θ from 0° to 360°, while the vertical axis D shows the depth information from the scanning cone. The zero frequency position, which is equivalent to the equal path length between the sample and the reference arm, is defined as D=0. Thus, the image shown in FIG. 1b can be thought of as a slice of the optic disc peeled off the circumference and laid flat into a rectangular skin.

Figure 2:
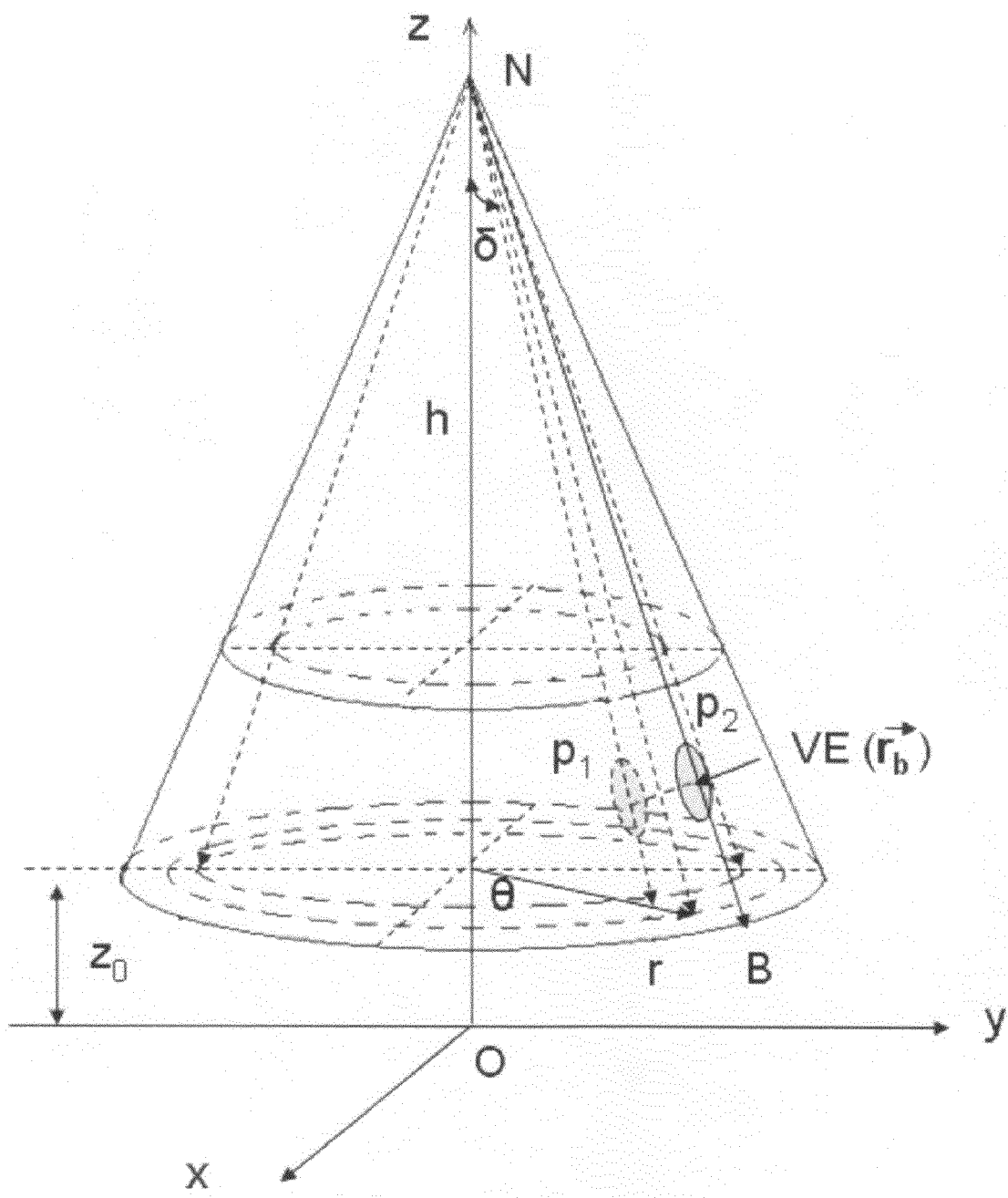
FIG. 2 shows an exemplary three dimensional diagram representation of OCT beams scanning circularly across the retina. Two scanning radii are shown in this diagram.

Referring to FIG. 2, there is shown a three dimensional diagram of the circular scanning pattern, where the retina is scanned circularly by the probe beam at radius $r_1$ and $r_2$. A small difference in the radii $\Delta r_0 = r_2 - r_1$ is chosen so that the blood vessel (VE) between the scanning circles may be approximated by a linear shape. In the coordinate shown in FIG. 2, the two positions of the blood vessel VE on the two scanning cones have the coordinates $P_1(r_1, \theta_1, z_1)$, and $P_2(r_2, \theta_2, z_2)$, respectively. Accordingly, the vector of the blood vessel can be expressed in terms of the coordinates as $\vec{r}_b (\Delta x = r_1 \cos \theta_1 - r_2 \cos \theta_2, \Delta y = r_1 \sin \theta_1 - r_2 \sin \theta_2, \Delta z = z_1 - z_2)$. In OCT images, the structure of the retina is matched to a coordinate system defined by (θ, D), as shown in FIG. 1b. The blood vessel VE has relative positions $(\theta_1, D_1)$ and $(\theta_2, D_2)$ in the two OCT images corresponding to the two different radii. According to FIG. 2, the value of Δz can be deduced from the image by relating the difference between the vessel's D coordinate $\Delta D = D_1 - D_2$ to Δz as:

$$\Delta z = \Delta D \cos \delta - (\sqrt{r_2^2 + h^2} - \sqrt{r_1^2 + h^2}) \cos \delta \quad (2)$$

where h is the distance from the nodal point to the retina, δ is the angle between the scanning beam and the rotation axis NO, as shown in FIG. 2. With equation 2, the vector of the retina blood vessel which is crossed by two scanning circles can be determined.

During scanning, the probe beam BN is on the scanning cone. The nodal point N has a coordinate of $(0, 0, h+z_0)$, where $z_0$ is the distance between the retina and the XY plane (in FIG. 2). For OCT scans at radius r, when the probe beam scans to the angle θ, the scanning point B on the retina will have a coordinate (r cos θ, r sin θ, -h). Thus, the vector of the scanning beam BN is $\vec{s}$ (r cos θ, r sin θ, -h). Having determined the values of vectors $\vec{s}$ and $\vec{r}_b$, one can then apply vector calculus to deduce the angle α between the OCT probe beam and blood flow as follows:

$$\cos \alpha = (\vec{r}_b \cdot \vec{s}) / (R_b R_s)$$

$$R_b = \sqrt{\Delta x^2 + \Delta y^2 + \Delta z^2}$$

$$R_s = \sqrt{r^2 + h^2} \quad (3)$$

where $R_b$ is the length of the vector $\vec{r}_b$, and $R_s$ is the length of vector $\vec{s}$. Because the difference in radii between the two scanning circles is small, the radius r in equation (3) can be approximated as $r = (r_1 + r_2)/2$. After the angle between the scanning beam and the blood vessel is determined, the real flow speed can be determined using the measured Doppler signal for the volumetric flow calculation.

Figure 3:
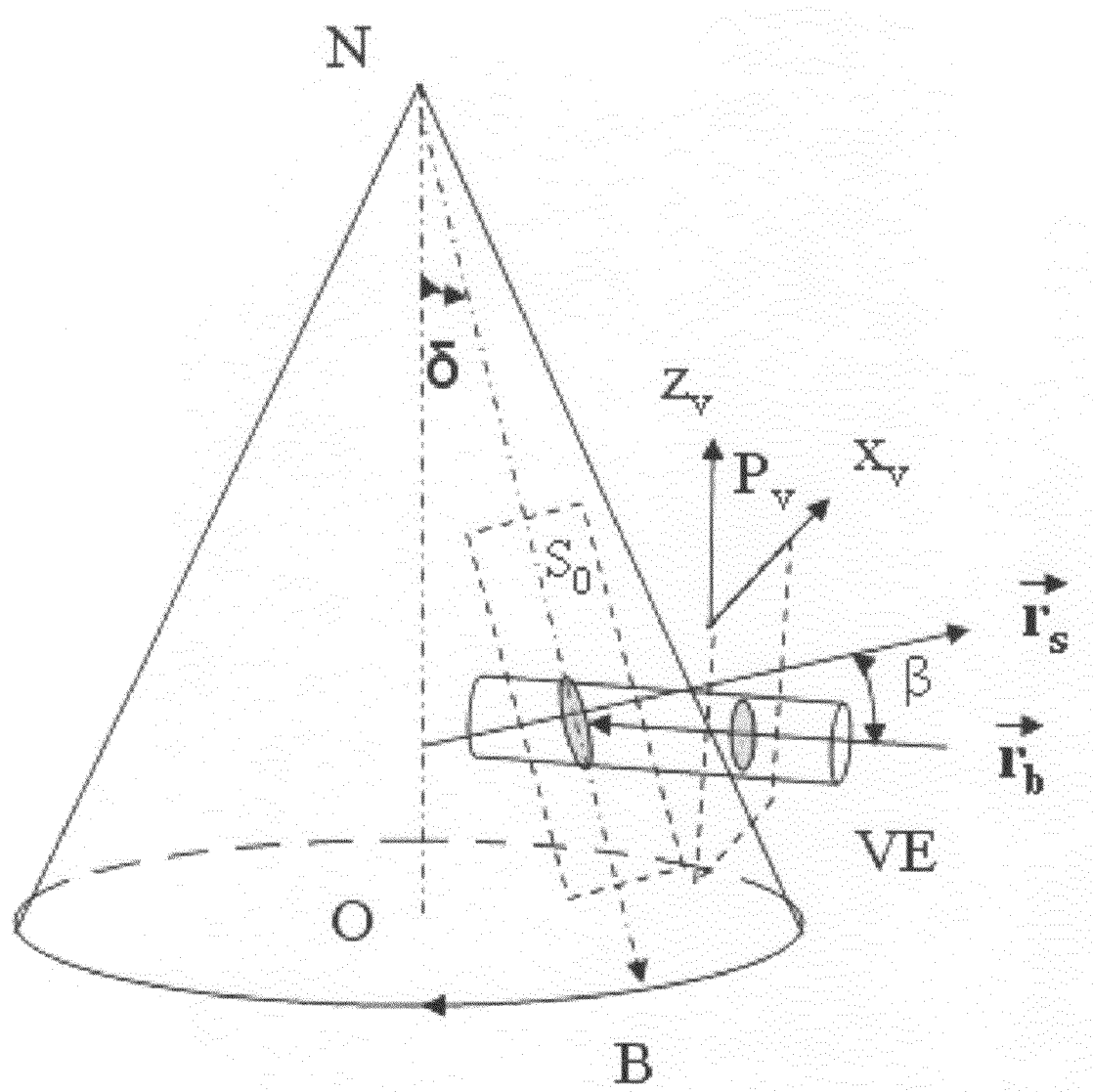
FIG. 3 shows an exemplary representation of the spatial relationship between the OCT beam and a vessel being scanned. The angle β between the OCT plane $S_o$ and the plane normal to the flow direction $P_v$ is indicated.

When considering the cardiac cycles, the speed of the blood flow can be expressed as $$V(x_v, z_v, t) = A_p(x_v, z_v) P(t) \tag{4}$$

where $A_p(x_v, z_v)$ is the speed distribution of the blood flow at the peak moment in the cardiac cycle in the cross section $P_v$ that is normal to the blood vessel, as shown in FIG. 3. $P(t)$ describes the variation in flow speed over the cardiac cycle normalized to 1 at the peak. Using the speed expression in equation 4, the volumetric flow $\overline{F}$ can be calculated as $$\overline{F} = \int\int A_p(x_v, z_v) dx_v dz_v \cdot \frac{1}{T}\int_0^T P(t) dt \tag{5}$$

where T is the period of pulsation.

To determine the real volumetric flow in the blood vessel, the integration should be done in the plane $P_v$ that is normal to the blood vessel (flow) direction. But in practice, the sampled Doppler FD-OCT plane $S_0$ (shown in FIG. 3) that crosses the blood vessel is different from plane $P_v$ in most cases, or we would not have a Doppler signal. The relationship between area size $\sigma_s = r\Delta\theta\Delta D$ in the OCT plane $S_0$ and area size $\sigma_v = \Delta x_v \Delta z_v$ in the plane $P_v$ is $\sigma_v = \sigma_s |\cos\beta|$, where $\beta$ is the angle between planes $P_v$ and $S_0$. If the angle $\beta$ can be determined, the retinal blood flow $\overline{F}$ can be calculated as $$\overline{F} = k|\cos\beta| \sum_S r A_p \Delta\theta \Delta D \tag{6}$$

$$k = \frac{1}{T}\int_0^T P(t) dt$$

where k is the pulsation factor. With the introduction of angle $\beta$, the integration for the flow calculation can be done within the vessel region S in the sampled Doppler FD-OCT image directly. According to vector calculus, the angle between two planes is the same as the angles between the two vectors normal to each of the planes. For $P_v$, the vector which is perpendicular to it is flow vector $\vec{r}_b$. As shown in FIG. 3, the FD-OCT plane $S_0$ is on the scanning cone. The unit vector $\vec{r}_s$ which is perpendicular to plane $S_0$ is in the plane determined by probe beam NB and rotation axis NO, and perpendicular to NB. The unit vector $\vec{r}_s$ can be deduced as $(\cos\delta\cos\theta, \cos\delta\sin\theta, \sin\delta)$, where $\delta$ is the angle between NB and NO in FIG. 3. With $\vec{r}_b$ and $\vec{r}_s$, the angle $\beta$ can be calculated as $$\cos\beta = (\vec{r}_s \cdot \vec{r}_b)/R_b \tag{7}$$

Given the above parameters and the exemplary algorithms for determining the values for the parameters from the OCT scans of the two planes, one skilled in the art will have in his possession a strategy for implementing various methods and systems of Doppler OCT based blood flow measurements as will be further illustrated with the following exemplary embodiments.

EXEMPLARY EMBODIMENTS

The above theoretical discussion outlines a framework for devising the various embodiments of the present invention. In general, embodiments of the present invention provide efficient and effective approaches to measuring blood flow by Doppler optical coherence tomography. By taking multiple OCT scans and analyzing the scans in accordance with the strategies of the present invention, one may obtain the necessary parameters to arrive at a blood flow measurement in a fast, accurate, and non-invasive manner.

Figure 9:
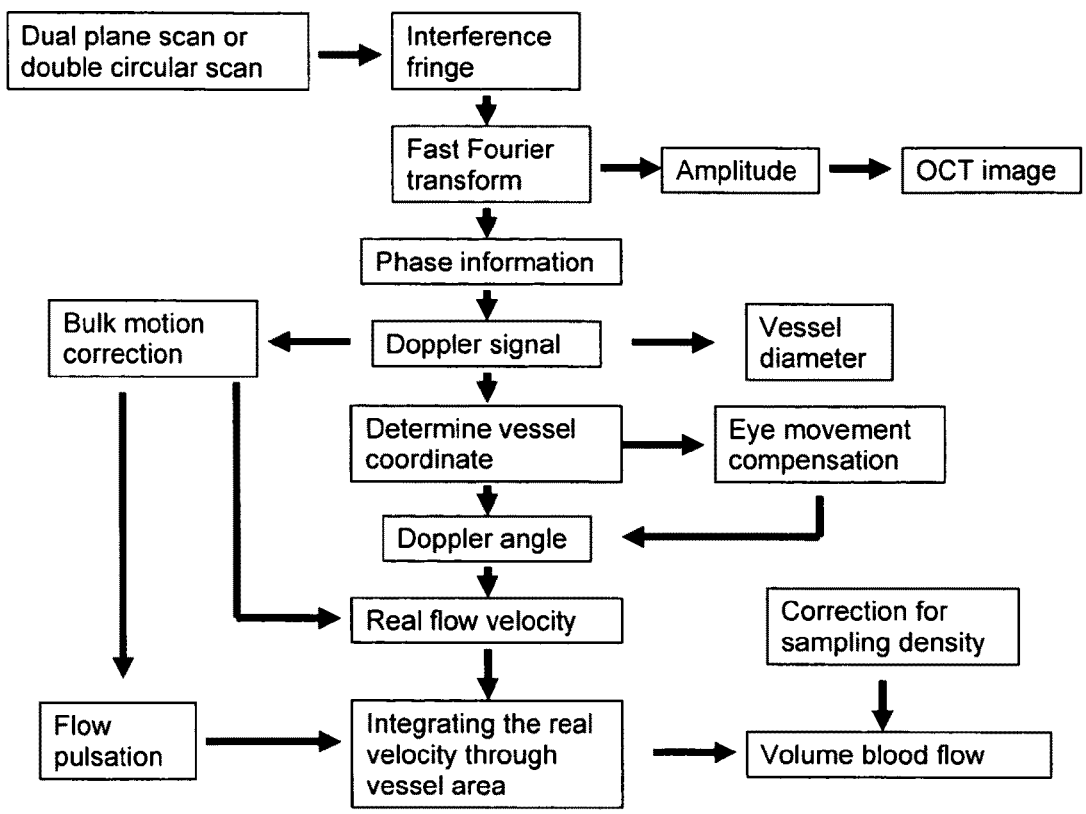
FIG. 9 shows a flowchart representation of a method in accordance with embodiments of the present invention.

In one preferred embodiment, a dual plane scanning technique is employed to obtain Doppler signals at two planes with small displacement. FIG. 9 shows a flowchart representation of this embodiment.

Figure 6:
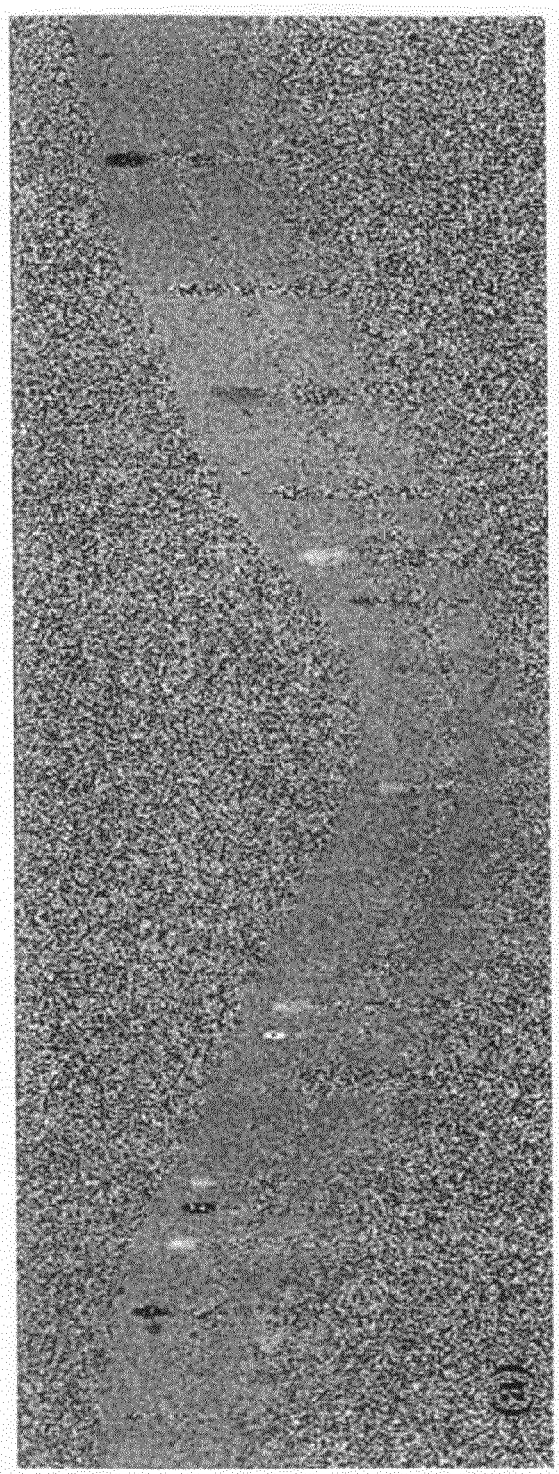
FIG. 6 shows exemplary Doppler OCT images with grayscale display of the Doppler frequency shift. The horizontal axis shows the scanning angle from 0 to 360 degrees; (a) Circular scan at a radius of 1.7 mm; (b) Circular scan at 1.9-mm radius. Retinal branch veins are labeled from $V_1$ to $V_7$.
Figure 6:
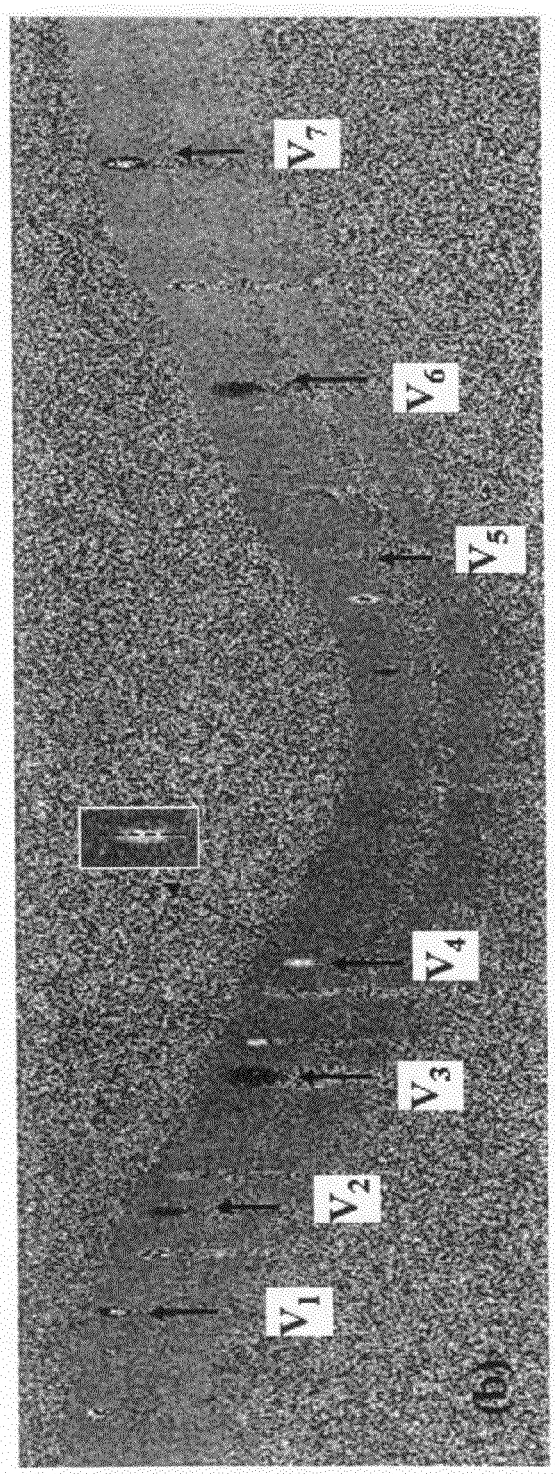

Referring to FIG. 9, a dual plane scanning pattern such as double circular scanning pattern (FIG. 4a) is used to scan the area of interest in a subject. In a Fourier domain optical coherence tomography setup, the interference signals from the scans are processed by fast Fourier transform to yield information about the amplitude and phases of the signals. The amplitude of the Fourier transformed spectra is then used to construct an OCT image of the physiological structure of the scanned area. The phase information is used to derive Doppler shift signals in the scan. One exemplary method of deriving a Doppler shift image is by comparing the phase differences of axial scans separated by regular intervals (e.g., every other axial scan). FIG. 6 shows an exemplary image representing the Doppler shift signals. From the Doppler shift images, one can then identify blood vessels and arrive at estimates of the diameters of the vessels (the blood vessels seen in these images are actually cross-sections of the vessels intersecting the scanning plane).

Using two Doppler shift images representing the two parallel scanning planes, one can then assign coordinates to the blood vessels. This way, each blood vessel will have two sets of coordinates corresponding to each scanning plane. These two sets of coordinates each define an end point of the segment of blood vessel between the two scanning planes. Therefore, these two sets of coordinates, together with the sign of the Doppler shift at the coordinate, define a vector for the blood vessel and direction of flow in the vessel.

At this juncture, correction for bulk motion and/or tissue movement (e.g. eye movement in ocular scans) can be optionally applied. Any commonly known correction algorithms may be suitably applied.

Once vectors for the blood vessels are determined, incident angles between the scanning beam and the vessels (Doppler angle) can be readily calculated from the angles between the incident scanning beam vector and the vessel vector. Armed with knowledge of the Doppler angle for a blood vessel, the real blood flow rate through the vessel is then determined.

To arrive at volume blood flow (the amount of blood flow per unit time averaged over a cardiac cycle), one may optionally calculate a pulsation factor as explained in equation (6). Other algorithms of integrating fluid flow known in the art may also be suitably used.

Figure 5:
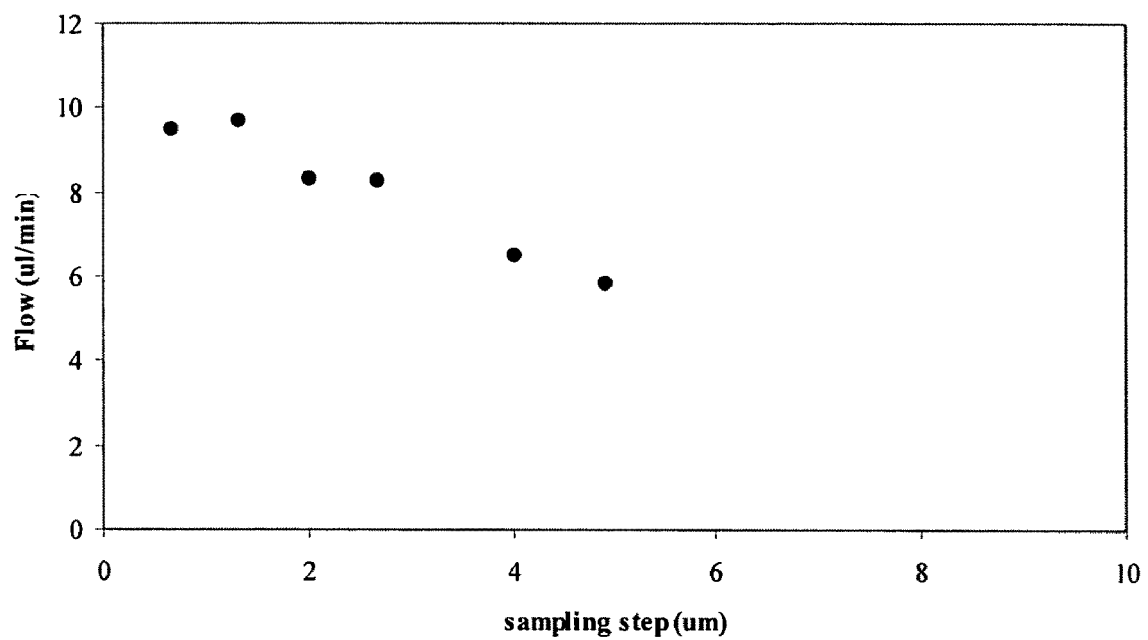
FIG. 5 shows the influence of sampling step on the measured volume blood flow.

Finally, a sampling density correction factor may be optionally applied to the volumetric flow. Here the sampling density refers to the step size between the consecutive axial scans. If the density of the axial scans is too high, the scan may take too long to complete. On the other hand, if the density is too low, the Doppler shift calculated by comparing two sequential scans may not be accurate. Thus, one must strive a balance between accuracy and speed. To allow a faster scanning speed without substantial loss of accuracy, inventors of the present invention have invented a method of correcting for the error due to lower sampling density. In one exemplary embodiment, a standard curve of flow versus sampling step size (such as shown in FIG. 5) is first constructed. A correction factor is then extrapolated from the curve and applied to the volumetric flow rate.

Accordingly, in one aspect, the present invention provides a method for measuring in vivo blood flow in a predefined region of a subject using Doppler Fourier domain optical coherence tomography. Methods in accordance with the embodiments of the present invention generally include the steps of (1) scanning a region in a subject with a scanning pattern that includes at least two planes to obtain OCT data; (2) analyzing the obtained OCT data to determine Doppler shifts and Doppler angles for each of the blood vessels; and (3) determining a volumetric blood flow rate using the Doppler shifts and Doppler angles.

The scanning patterns are not particularly limited. It will be understood by those skilled in the art that the choice of the scanning pattern will depend on the location, the type of tissue/organ, and other factors. For example, circular patterns are particularly suited for scanning retina blood flows. Linear patterns may be suited for scanning regions in which consideration of only linear blood flows is sufficient (e.g. finger tips). Other regions accessible to Doppler Fourier optical coherence tomography, such as GI track, skin, etc., may also be suitably measured by methods of the present invention.

In general, scanning patterns should comprise at least two planes that are substantially parallel. The term "substantially" as used herein means that the deviation from parallel is within the relative error of the scanning machine and the desired measurement accuracy. For example, FIG. 4b shows a dual parallel plane scanning pattern in which the two parallel planes intersect the same blood vessel (left). The Doppler angle and the vector of the blood vessel can be easily extrapolated from the Doppler image (right) using methods of the present invention. FIG. 1-3 dual circle scanning pattern traced out by a single scanning beam rotated through a nodal point. The resulting scanning planes are conic in shape, hence, they are not perfectly parallel. However, when the distance between the two planes is small compare to the distance between the nodal point and the retina, the deviation from true parallel is also small. In a typical dual circle retina scan, the distance between the two planes is preferably about 0.2 mm and the distance between the nodal point and the retina is preferably about 17 mm. This will give a ratio of about 0.2/17 (or ~1%). Thus, for all practical purposes, such minor deviations are also within the meaning of "parallel" in the context of the present invention.

In some embodiments, scanning patterns that have the planes circumscribing a region of interest is preferred. Such scanning pattern will have the benefit that all blood vessels entering and leaving the region will be accounted for within a single scan. It is also preferred that the chosen scanning pattern is capable of being completed within a single cardiac cycle. Preferably, the scanning pattern will yield a scanning frame rate of 4 Hz or higher.

The distance between the scanning planes are preferably small so that segments of blood vessels between the two planes may be approximated by straight lines. Preferably, the distance is from about 100 µm to about 300 µm, more preferably less than 300 µm.

In some further embodiments, steps for correcting sampling density artifacts and bulk movement artifacts may also be included. The various embodiments can all be automated by computers. An exemplary automation may be a computer configured with software instructions to perform the method steps according to FIG. 9. Development of such software is within the skill of the art. Exemplary implementation may be achieved using programming languages such as C/C++, JAVA, or any other software development tool commonly known in the art.

Methods of the present invention are generally applicable to any multi-cellular organisms with a circulatory system. Accordingly, the term "subject" as used herein encompasses all multi-cellular organisms with a circulatory system that are amenable to optical coherence scanning. Exemplary subjects may include mammals, avian species, or any other organisms whose physiology is based on actively pumped circulatory systems.

In another aspect, the present invention provides a system for measuring and/or monitoring local blood flow in a subject that is indicative of a diseased condition. Systems in accordance with embodiments of the present invention generally include an optical coherence tomography instrument, and a processing unit configured to perform methods of the present invention as set forth above.

Exemplary diseases and diagnostic applications may include ophthalmological conditions (e.g., glaucoma), cardiac conditions (e.g. vein occlusions), dental conditions, or conditions of the GI track, but are not limited thereto.

Figure 10:
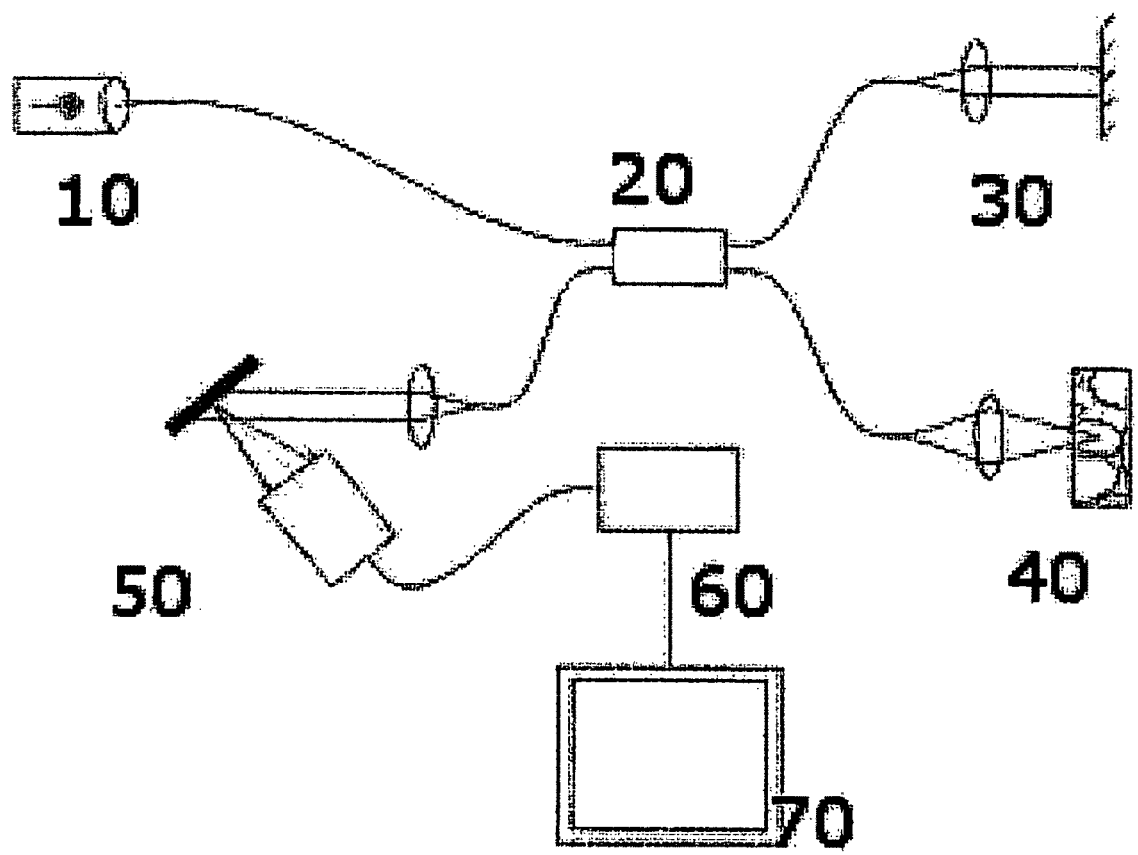
FIG. 10 shows a block diagram representation of an exemplary system in accordance with embodiments of the present invention.

FIG. 10 shows an exemplary system in accordance with embodiments of the present invention. Referring to FIG. 10, an optical coherence tomography instrument generally has a low coherence light source 10 being guided by a light conducting medium such as fiber optics. The source light is split up by a beam splitter 20 into a reference beam forming the reference arm 30 of the instrument and a sampling beam forming the sampling arm 40 of the instrument. The interference signal is detected by a scanning camera 50. The detected signal is then processed by a processing unit 60, the results of which may then be displayed to a user on a display 70.

In one embodiment, the processing unit is configured to perform digital signal processing, including fast Fourier transform, and methods of the present invention as set forth above.

The processing unit may be any suitable computer system commonly known in the art, including general purpose PC, or custom designed electronics, but are not limited thereto. Methods of the present invention may be hard coded into the hardware or may be provided in the form of software encoded on a computer readable medium such as harddrive, read-only memory, CD, DVD, or any other computer readable medium commonly known in the art.

Having generally described this invention, a further understanding can be obtained by reference to certain specific examples which are provided herein for purposes of illustration only and are not intended to be limiting unless otherwise specified.

EXAMPLES

Materials and Methods

Experimental Setup

The spectrometer-based Doppler FD-DOCT system employed in this experiment contains a superluminescent diode with a center wavelength of 841 nm and a bandwidth of 49 nm. The measured axial resolution was 7.5 µm in air. Considering the refractive index of tissue, the axial resolution would be 5.6 µm in tissue. The transverse resolution was about 20 µm as limited by optical diffraction of the eye. Light from the source travels through an 80/20 coupler with 80% of the source power entering the reference arm of a standard Michelson interferometer and 20% entering the sample arm. The sample arm contains a standard slit-lamp biomicroscope base that has been adapted with custom OCT scanning optics. Power incident on the cornea is 500 µW, which was well below the ANSI limits for extended beam exposure. Reference and sample arm light interfere in the fiber coupler and the composite signal is detected by a custom spectrometer. The spectrometer contains a 1024 pixel line-scan camera. Data from the camera is transferred via the Cameralink interface to a high-end PC. The measured SNR was 107 dB at 200 μm from the zero-path length difference location. The time interval τ between two sequential A lines is 56 μs (with an integration time of 50 μs, and a data transfer time of 6 μs). The maximum determinable Doppler shift was 8.9 Khz without phase unwrapping, yielding a maximum velocity component in the eye (n=1.33) of 2.8 mm/s. The measured minimum determinable speed was 16.3 μm/s due to phase noise.

Image Sampling and Processing

Figure 4A:
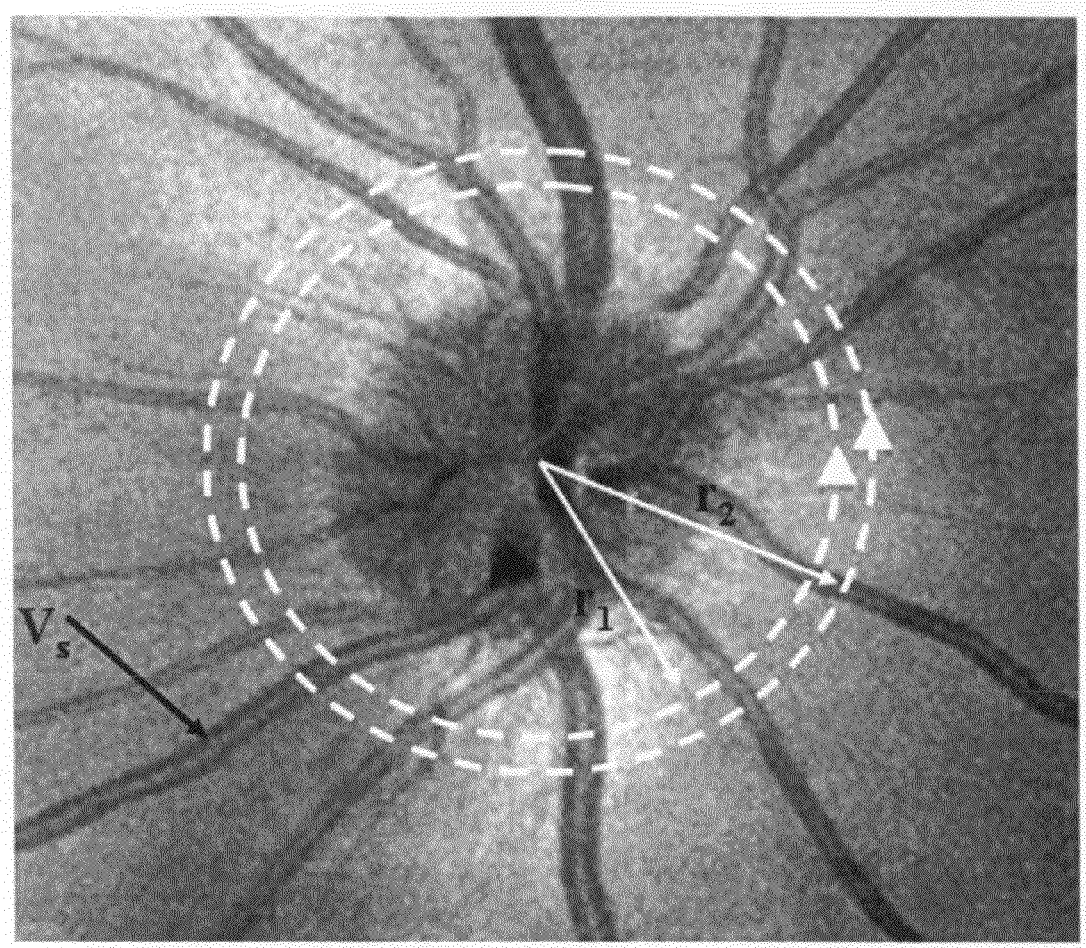
FIG. 4a shows an exemplary path of the scanning beam in the double circular scanning pattern; 4b shows an exemplary path of the scanning beam in two short parallel lines, resulting in two parallel scanning planes.
Figure 4B:
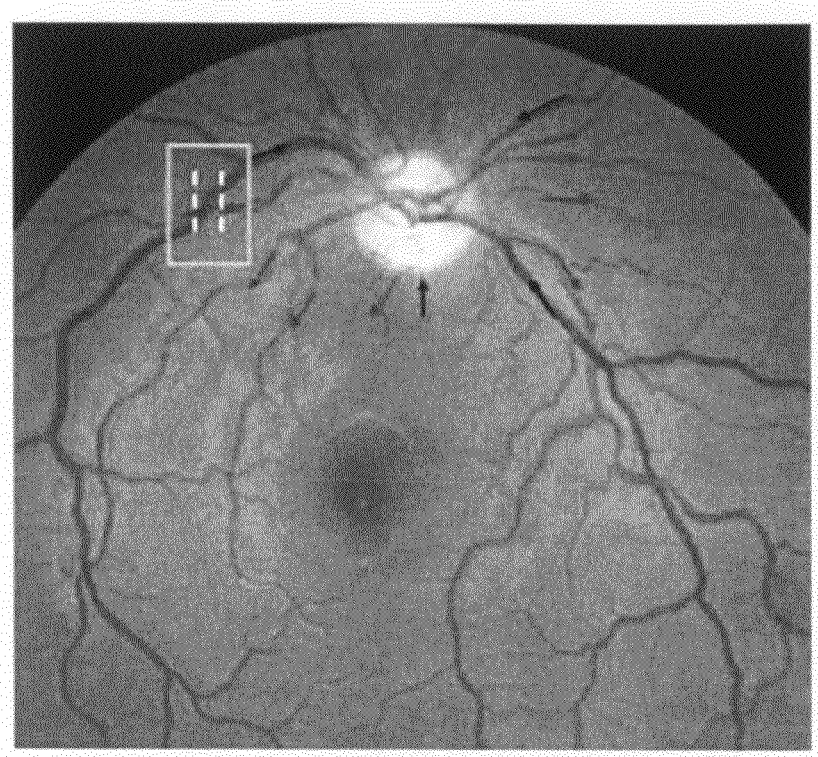
Figure 4B:
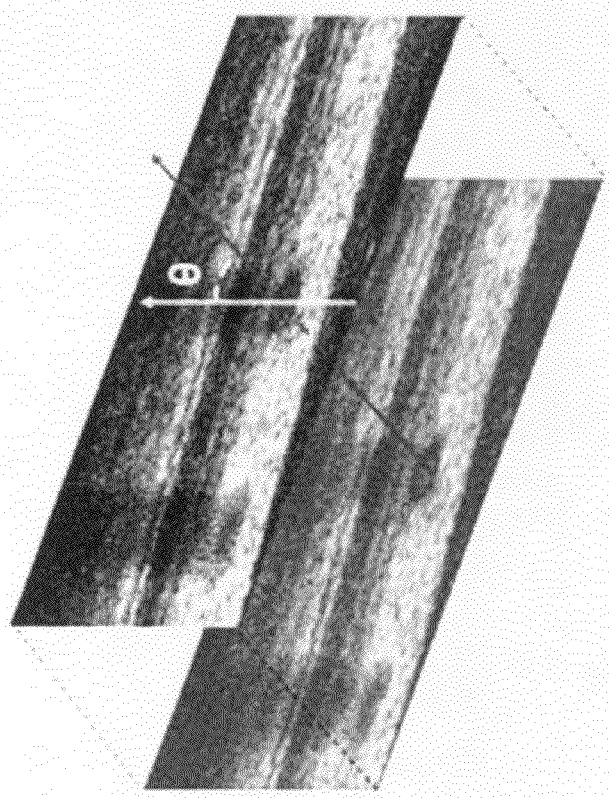

The FD-OCT probe beam was scanned on the retina around the optic nerve head at radii $r_1$ and $r_2$ repeatedly, as shown in FIG. 4a. There were 3000 A-lines sampled in each circle. The phase differences for every three A-lines were calculated to get the Doppler frequency shift. So each frame consisted of 1000 vertical lines. The frame rate for Doppler ED-OCT imaging was 4.2 frames per second for real time display. There were four pairs of (total of eight) Doppler FD-OCT images sampled for each flow measurement for a total recording time of approximately 2 seconds.

The sampled Doppler FD-OCT images were saved for data processing. There were four Doppler images sampled at radius $r_1$. The other four images were sampled at radius $r_2$. The coordinates of a single retina vessel in those four Doppler images sampled at radius $r_1$, were averaged as $(\theta_1, D_1)$. The coordinates of the same vessel in the other four Doppler images were sampled at radius $r_2$, and were averaged as $(\theta_2, D_2)$. The averaged coordinates $(\theta_1, D_1)$ and $(\theta_2, D_2)$ are used to calculate the angle α and β based on equations (3) and (7). The distance h from the nodal point N to the retina surface was chosen as 18 mm. The speed profile of a single vessel in the eight Doppler images was calculated. Peak velocity in the eight flow profiles was normalized to the maximum one and plotted against time to show the flow pulsation. This curve was integrated as the pulsation term k in equation (6). The maximum flow speed profile of the eight analyzed flow profiles was put in equation (6) as $A_p$, to calculate the retinal blood flow (F). For some venules, the Doppler flow signal was too weak for an accurate reading at diastole (minimum flow portion of the cardiac cycle). The pulsation factor k in the adjacent venules was used instead for flow calculation.

Influence of Sampling Density

In Doppler OCT, the phase difference between sequential axial scans is calculated to determine Doppler frequency shift. Ideally, the phase difference should be compared at the same location. But for retina OCT system, the probe beam scans continuously across the retina and there is a small displacement between sequential axial scans. If the sampling locations were not sufficiently close (relative to the beam diameter), phase decorrelation would decrease the measured Doppler shift [13]. To evaluate the influence of sampling step on flow measurement, the inventors measured the volume flow for the vessel $V_s$ (FIG. 4a) at different sampling steps with dual scanning plane method [15]. The scanning length was 1 mm. The flow at each sampling step was measured three times and averaged. The result is shown in FIG. 5, where the horizontal axis is the sampling step, and the vertical axis shows the measured volume blood flow. It can be seen that measured blood flow decreased with increasing sampling step. This decrease was noticeable starting at the sampling step around 1.4 μm. Therefore, to avoid the influence of phase decorrelation between adjacent axial scans, the sampling step should be shorter than 1.4 μm. In this FD Doppler OCT system, the inventors chose 3000 axial lines sampling density for real time display at 4.2 Hz. At a scanning radius of 1.9 mm (circle length 11.93 mm), the sampling step was about 4.0 μm. From FIG. 5, it can be seen that the ratio between the measured flow at 4.0 μm and 0.7 μm step is 0.683. Because the phase decorrelation between adjacent axial lines is mainly related with the beam spot size on the retina [13], which is a system factor, the inventors can use the curve in FIG. 5 to correct the measured flow result for a fixed sampling step.

Results

The in vivo retinal flow measurement was performed on the right eye of the first subject. A green cross fixation target was used to direct the scanning position and reduce the subject's eye movements. FIG. 6 shows the Doppler FD-OCT images recorded in the inventors' experiment using the circular scanning protocol, with $r_1$=1.7 mm and $r_2$=1.9 mm. The blood flow within major blood vessels distributed around the optic nerve head that are visible in these images.

The inventors chose to measure retinal blood flow in the branch veins rather than arteries because the arteries have higher flow velocities, which can cause excessive phase wrapping and signal fading. The identification of branch veins among the other vessels distributed around the optic nerve head was based on the recorded Doppler frequency shift and the calculated angle between the probe beam and blood vessel. According to equation (1), the flow that occurs in different directions in the same blood vessel will introduce different frequency shifts in the back-scattered beam. When the flow is moving away from the probe direction, cos α>0, and the scattered light will have a negative frequency shift. When the flow is toward the probe beam, cos α<0, and the scattered light will have a positive frequency shift. Thus, from the calculated angle α and the sign of the frequency shift, the direction of flow in the blood vessel can be determined. Knowing the direction of flow can help separate the veins from the arteries that are distributed around the optic disk because arteries have a direction of flow towards the retinal periphery from the nerve head, and veins have a direction of flow towards the nerve head from the peripheral retina.

The Doppler information retains motion artifacts from motion of the human retina and scanning noise of the OCT system. Doppler noise due to background motion is larger than the phase instability of the system and will influence the measurement results if uncorrected. In the lateral direction of Doppler image (FIG. 6), the Doppler signals are sampled at different time. Some parts are dark, some parts are bright. Therefore, the background motion signals at different horizontal positions are not correlated. Motion effect can be considered and corrected in a local area.

Figure 7:
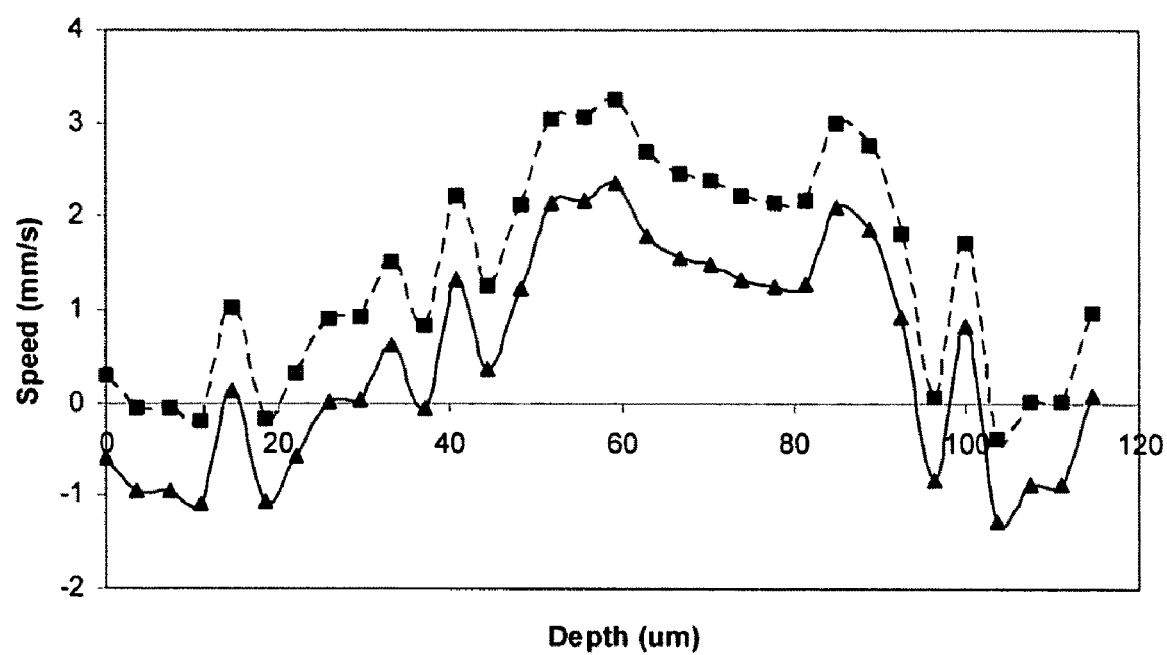
FIG. 7 shows correction of the Doppler noise due to background motion.

Considering the vessel $V_4$ (enlarged into the white window in FIG. 6b), for each axial line, the Doppler signal between the inner retina boundary and vessel boundary was averaged. This value is the Doppler signal due to the local tissue motion. This motion value will be subtracted from the Doppler signal in the whole axial line to get the real signal induced by blood flow. FIG. 7 shows one axial line Doppler signal before and after background removing. The position of the Doppler signal shows as the dashed line in FIG. 6b. The averaged tissue motion speed is −0.89 mm/s. In FIG. 7, the solid curve shows the original signal. The dashed curve shows the Doppler signal after background removal. It can be seen that after subtracting the motion signal, the background speed was close to zero. Then, the integration can be done near the vessel area to get the volumetric flow without the need to search the vessel boundary.

Figure 8:
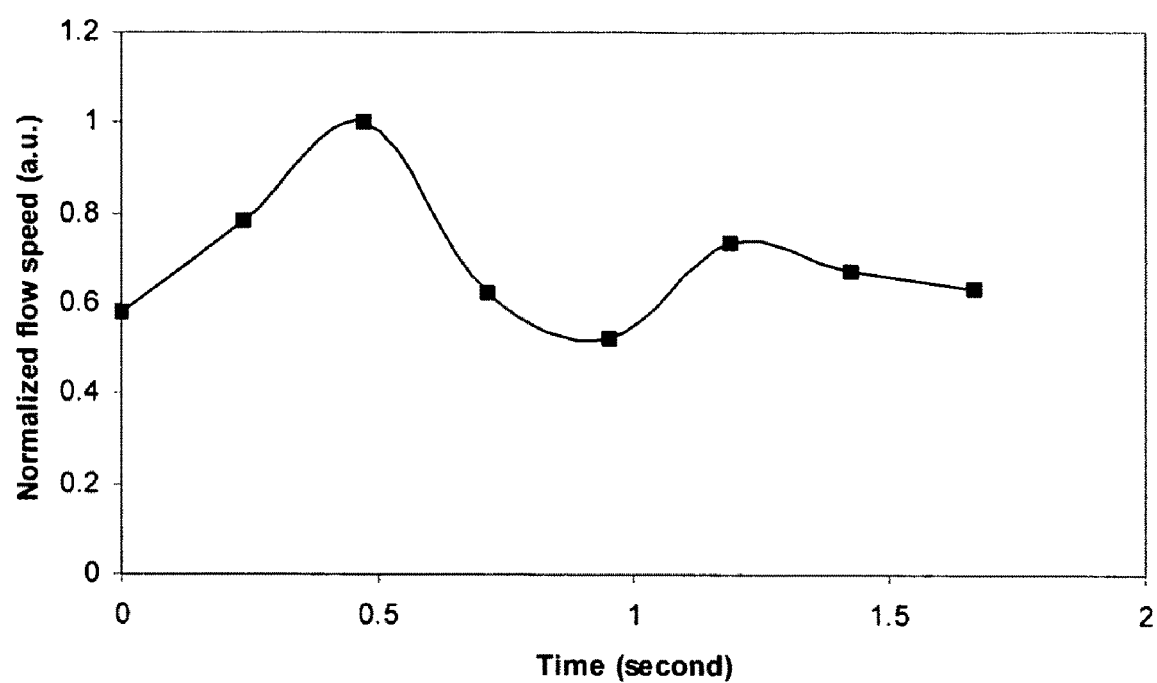
FIG. 8 shows normalized peak flow speed variation with time for the vessel $V_1$ shown in FIG. 6.

The first vessel $V_1$ as shown in FIG. 6b had a negative frequency shift with positive phase wrapping at the center. After phase unwrapping, the flow profile A(θ, D) was obtained. The measured positions of $V_1$ in two sequential Doppler OCT images were ($\theta_1$=37.60, $D_1$=−307.1 μm) and ($\theta_2$=37.80, $D_2$=−255.3 μm). The vector of the blood vessel was calculated as $P_1P_2$ (−154, −128, −71.34). From equation (3), the angle between the scanning beam and blood vessel was calculated as cos α=0.24, and α=76.10. Since the signal had a negative frequency shift and cos α>0, the direction of the flow in $V_1$ should be moving from $P_2$ to $P_1$. In our scanning pattern, $P_1$ is on the inner cone closer to the nerve head while $P_2$ is on the outer cone. Thus, this flow is toward the optic disk, and blood vessel $V_1$ is a vein. Through continuous scanning, 8 frames of the Doppler signals were recorded. The flow speed at the center part of vessel $V_1$ shown in FIG. 6b was analyzed. FIG. 8 plots the normalized flow speed of vessel $V_1$. The pulse factor was calculated based on the curve in FIG. 8 as k=0.695. With the value of cos α, the calculated peak flow speed in $V_1$ was 17.0 mm/s. From equation (7), the angle β was calculated as cos β=−0.97. With these parameters, the volumetric flow in vessel $V_1$ was calculated as 3.01 μl/min. Considering the effect of phase decorrelation due to insufficient sampling density (FIG. 5), the real volumetric flow was 4.41 μl/min.

The flow directions of the main vessels around the optic nerve head were similarly analyzed, and the main venules were identified and labeled $V_1$ to $V_7$ shown in FIG. 6b. The blood flow for each venule was calculated and shown in Table 1. The summation of these flows determined the total venous flow out of the retina, which was 53.87 μl/min. The measured scanning angle between the probe beam and blood vessel is also shown in Table 1.

There were 7 measurements performed in this experiment in which the total venous flow was calculated for each measurement. The averaged total flow was 52.90 μl/min. The standard deviation was 2.75 μl/min, which is about 5.2% of the average flow. The average flow and standard deviation for each venule are shown in Table 2. It can be seen that the flow coefficient of variation in a single vessel is larger than that of the total flow. This means the total retinal blood flow tends to be stable, but the flow distribution inside the retina fluctuates. This result shows fast sampling DCSP method has the advantage to measure the dynamic property of flow distribution in the retina, which is hard to detect through sequentially imaging each retinal blood vessel individually due to long sampling time.

To test the reliability of this method, another subject was measured. The left eye of the subject was scanned 6 times. Each scan was finished within 2 seconds in which 8 Doppler FD-OCT frames were acquired. The scanning radii were $r_1$=1.8 mm and $r_2$=2.0 mm. Through similar data analysis, there were a total of 5 main venules identified from the Doppler image. By analyzing the 6 sets of sampled data, the average flow was 45.23 μl/min. The standard deviation of the total flow was 3.18 μl/min, which was 7.0% of the average flow of the second subject. The average flow for both subjects was 49.07 μl/min with a difference of 7.67 μl/min.

Discussion

This Example demonstrates that the total retinal blood flow can be determined when a rapid data acquisition time is utilized. The dynamic retinal flow distribution can also be detected. The measurement can be used to detect abnormal retinal blood flow and determine if a particular treatment returns the total flow back to normal levels. The inventors targeted the major branches of the central retinal veins because their size and velocities are within the dynamic range of the Doppler FD-OCT system. Because the total venous flow volume is identical to that of arteries in the retina, as shown by Riva and colleagues [18], measuring the total venous flow alone is sufficient to quantify the total retinal blood flow. The measured average total venous flow was approximately 52.9 μl/min and 45.23 μl/min for the two subjects, which was comparable with the reported total venous flow of 34±6.3 μl/min by laser Doppler velocimetry [18].

There were some limitations in this particular exemplary embodiment. Multiplied by the high sampling density necessary to capture the retinal blood vessels, a large number of axial scans are needed in each circle. This reduces the frame rate of the Doppler FD-OCT. Our frame rate of 4.2 Hz was barely fast enough to track the variation in flow velocity during the cardiac cycles (FIG. 8). While not wanting to be bound by the theory, the inventors believe a higher frame rate would improve the accuracy of the measurements. Secondly, the transverse sampling interval of 4.0 μm (scanning diameter of 1.9 mm for 3000 axial sampling lines) was not sufficient to avoid phase decorrelation in the adjacent axial lines. A measured correction factor had to be used to calculate the volume retinal flow. At the same time, the venules with diameter less than 65 μm were not taken into account due to less lateral sampling density. Yet, an even finer sampling interval could remove the phase decorrelation effect and detect even smaller vessels and increase the accuracy of our measurement of blood flow. Thirdly, the Doppler velocity was unreadable due to the fading of OCT signals that occurred in some arteries during systole. The inventors believe this is due to the velocity-related interferometric fringe washout—if the reflector moves by more than a quarter wavelength within the spectrometer's integration time of 50 μs, the peaks and troughs of the interference signal average out. Fourthly, at high flow speeds, the Doppler phase shift can exceed π, causing "phase wrapping." The inventors' phase unwrapping algorithm can only analyze to one period of phase wrapping. A very high flow that causes phase wrapping over one period is too complex for the computer software to analyze reliably. Thus, avoiding high period phase wrapping is desired for data processing. Finally, any eye motions during data sampling affects the accuracy of retinal vessel position and angle measurements. This is especially critical for blood vessels that are nearly perpendicular to the OCT beam, when a small position shift could greatly affect the flow measurement.

All of the above limitations can be lessened with a greater imaging speed. Decreasing the effective integration time of the spectrometer can increase the detectable range of flow speeds. A higher speed will also allow for a finer degree of sampling in time (more time points within each cardiac cycle) and space (more points sampled within each blood vessel). With the continual improvement in the speed of line cameras that make up the heart of the FD-OCT system, it is expected that these limitations will become less important over time.

In the inventors' preliminary work, the retinal blood flow measurement was demonstrated through sequentially imaging each retinal blood vessel individually. However, the data sampling was time consuming and precluded clinical measurement of total retinal blood flow. In the present invention, the fast data sampling (within 2 seconds) became practical with DCSP method to catch all the retinal blood vessels.

The present invention compares favorably to existing technologies that measure retinal blood flow [19-24]. Fluorescein angiography [21, 22] allows visualization of retinal hemodynamics, but does not measure volumetric blood flow. Pulsatile Ocular Blood Flowmeter (POBF, Paradigm Inc.) [19] assumes a scleral rigidity that relates intraocular pressure and eye volume. Coherence flow measurement technique [21] detects the interference pattern formed by laser light partially reflected by both the cornea and the retina to determine the fundus movement in micrometers. This movement is used as a surrogate for choroidal blood flow. There are two types of laser Doppler flowmeter (LDF) on the market: the Canon (Canon U.S.A., Inc.) and the Heidelberg (Heidelberg engineering, GMBH, Heidelberg Germany). Canon flowmeter (CF) was developed to measure the volumetric blood flow in absolute units [23, 24]. However, its accuracy is limited due to the lack of the information of the speed distribution across the blood vessel, and accurate vessel size. The flow volume calculation requires an assumed relationship between the maximum Doppler shift and the true average blood velocity. Furthermore, CF requires careful positioning of the scan across each blood vessel. Measuring the total retinal flow is a laborious and difficult process. The Heidelberg retina flowmeter (HRT) [25] is also based on the LDF principle. It utilizes a probe beam that repeatedly sweeps the fundus to detect the beat signal induced by the Doppler effect from blood flow. The HRT measures flow in the retinal capillary bed over a small region. Therefore measurement of the total retinal blood flow that reflects on the global health of the eye is not possible. Furthermore, the flow is measured in arbitrary units and the results can be affected by tissue reflectivity properties unrelated to flow [26]. Most of the existing methods measure retinal blood flow in arbitrary units because of the use of assumed parameters. These parameters may differ from eyes, persons and regions of measurement. Thus, it is difficult to make diagnostic comparisons using arbitrary measurement units. Direct measurement of total regional retinal blood flow in absolute physical units is more desirable for detection abnormally elevated or decreased perfusion in the retina.

Methods in accordance with embodiments of the present invention can be used to measure the angle of a blood vessel relative to a probe beam to derive the flow vector. They produce an absolute flow measurement by integrating the flow profile of the blood vessel cross-section without resorting to any assumptions on the anatomic or flow parameters. Flow pulsation was averaged over cardiac cycles. For most of the reported techniques for measuring blood flow, data sampling is time consuming. In the exemplary DCSP embodiment, with the data sampled within 2 seconds, the total retinal blood flow can be calculated. This will greatly reduce the chair time for the photographer and patient in the clinic. The dynamic retinal blood flow distribution can also be detected. This is believed to be the first description of a quick assessment of total fundus flow using a fast scanning pattern. The measured results in volume flow units can be compared for different subjects.

The measurement of total retinal blood flow is important for the treatment of many eye diseases. The leading causes of blindness in the U.S. [27-29], such as diabetic retinopathy and age-related macular degeneration, are related to vascular abnormalities. Central retinal vein occlusion and branch retinal vein occlusions are also common retinal diseases characterized by decreased retinal blood flow. Glaucoma is another leading cause of blindness that is primarily linked to elevated intraocular pressure. But poor circulation in the retina and optic nerve is thought to be a risk factor for glaucoma disease progression as well [30-34]. An accurate measurement of total blood flow with Doppler OCT could enhance our understanding of pathophysiology, develop treatments that improve retinal blood flow, and finally improve the diagnosis of many retinal and optic nerve diseases.

CONCLUSION

In summary, in vivo measurements of retinal blood flow using Doppler Fourier domain OCT are demonstrated in this example. A double circular scanning pattern was developed to determine the angle between the blood flow and scanning beam so the real flow velocity can be measured. Based on the direction of flow, venules can be distinguished from arterioles. Volumetric flow in each venule around the optic nerve head was integrated in the sampled cardiac cycles. The measured blood flow for two subjects was 52.9 and 45.23 µl/min with a difference of 7.67 µl/min. The present invention provides a method that measures total retinal blood flow that is fast, reproducible, and not dependent on any assumption of vessel size or flow profiles.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the appended claims.

TABLE 1

Vessel diameter, scanning angle, and flow volume for the retinal veins of first subject

| | Vessel | | | | | | |
|---|---|---|---|---|---|---|---|
| | $V_1$ | $V_2$ | $V_3$ | $V_4$ | $V_5$ | $V_6$ | $V_7$ |
| Diameter (µm) | 70.3 | 78 | 152 | 70 | 126 | 115 | 96 |
| Angle (degree) | 76.1 | 78.8 | 85.9 | 96.6 | 94.25 | 84.4 | 81.3 |
| Volume Flow (µl/min) | 4.41 | 2.88 | 13.89 | 3.50 | 9.94 | 11.58 | 7.67 |

TABLE 2

Repeatability for all the measured venules

| | Vessel | | | | | | | |
|---|---|---|---|---|---|---|---|---|
| | $V_1$ | $V_2$ | $V_3$ | $V_4$ | $V_5$ | $V_6$ | $V_7$ | Total |
| Average flow (µl/min) | 4.33 | 4.29 | 13.32 | 3.53 | 9.44 | 10.01 | 7.98 | 52.9 |
| STD | 0.69 | 1.64 | 0.95 | 0.85 | 1.17 | 2.08 | 1.32 | 2.75 |
| Coefficient of variation (%) | 16 | 38 | 7 | 24 | 12 | 21 | 17 | 5.2 |

REFERENCES

The following references are cited herein. The entire disclosure of each reference is relied upon and incorporated by reference herein.

1. D. Huang, E. A. Swanson, C. P. Lin, et al., Optical coherence tomography. *Science.* 254, 1178-1181 (1991).
2. M. R. Hee, C. A. Puliafito, C. Wong, et al., Optical coherence tomography of macular holes. *Ophthalmology.* 102, 748-756 (1995).
3. C. A. Puliafito, M. R. Hee, C. P. Lin, et al. Imaging of macular diseases with optical coherence tomography. *Ophthalmology.* 102, 217-229 (1995).
4. M. R. Hee, C. R. Baumal, C. A. Puliafito, et al. Optical coherence tomography of age-related macular degeneration and choroidal neovascularization. *Ophthalmology* 103, 1260-1270 (1996).
5. J. S. Shuman, M. R. Hee, C. A. Puliafito, et al., Quantification of nerve fiber layer thickness in normal and glaucomatous eyes using optical coherence tomography. *Arch Ophthalmol.* 113, 586-596 (1995).
6. J. S. Shuman, M. R. Hee MR, A. V. Arya, et al., Optical coherence tomography: a new tool for glaucoma diagnosis. *Curr Opin Ophthalmol.* 6, 89-95 (1995).

7. X. J. Wang, T. E. Milner, J. S. Nelson. Characterization of fluid flow velocity by optical Doppler tomography. *Opt lett.* 20, 1337-1339 (1995).
8. J. A. Izatt, M. D. Kulkarni, S. Yazdanfar, J. K. Barton, A. J. Welch, In vivo bidirectional color Doppler flow imaging of picoliter blood volumes using optical coherence tomography. *Opt Lett.* 22, 1439-1441 (1997).
9. Y. Zhao, Z. Chen, C. Saxer, S. Xiang, J. F. de Boer, J. S. Nelson. Phase resolved optical coherence tomography and optical Doppler tomography for imaging blood flow in human skin with fast scanning speed and high velocity sensitivity. *Opt Lett.* 25, 114-116 (2000).
10. S. Yazdanfa, A. M. Rollins, J. A. Izatt. In vivo imaging of human retinal flow dynamics by color Doppler optical coherence tomography. *Arch Ophthalmol.* 121, 235-239 (2003).
11. V. X. D. Yang, M. Gordon, E. S. Yue, et al. High speed, wide velocity dynamic range Doppler optical coherence tomography (Part II): Imaging in vivo cardiac dynamic of *Opt Express.* 11, 1650-1658 (2003).
12. S. Yazdanfar, A. M. Rollins, J. A. Izatt. Imaging and velocity of the human retinal circulation with color Doppler optical coherence tomography. *Opt Lett.*, 25, 1448-1450 (2000).
13. B. R. White, M. C. Pierce, N. Nassif, et al. In vivo dynamic human retinal blood flow imaging using ultra-high-speed spectral domain optical Doppler tomography. *Opt Express.* 11, 3490-3497 (2003).
14. R. A. Leitgeb, L. Schmetterer, C. K. Hitzenberger, et al. Real-time measurement of in vitro flow by Fourier-domain color Doppler optical coherence tomography. *Opt Lett.* 29, 171-173 (2004).
15. Y. Wang, B. A. Bower, J. A. Izatt, O. Tan, D. Huang. In vivo total retinal blood flow measurement by Fourier domain Doppler optical coherence tomography. *J Biomed Optics.* 12, 041215-22 (2007)
16. R. Leitgeb, C. K. Hitzenberger, A. F. Fercher. Performance of fourier domain vs. time domain optical coherence tomography. *Opt. Express.* 11, 889-894 (2003).
17. M. Wojtkowski, V. J. Srinivasan, T. H. Ko, J. G. Fujimoto, A. Kowalczyk, J. S. Duker. Ultrahigh-resolution, high-speed, Fourier domain optical coherence tomography and methods for dispersion compensation. *Opt Express.* 12, 2404-2422 (2004).
18. C. E. Riva, J. E. Grunwald, S. H. Sinclair, B. L. Petrig. Blood Velocity and volumetric flow rate in human retinal vessels. *Invest Ophthalmol Vis Sci.* 26, 1124-1132 (1985).
19. M. E. Langham, K. F. To'mey. A clinical procedure for the measurement of the ocular pulse-pressure relationship and the ophthalmic arterial pressure. *Exp Eye Res.* 27, 17-25 (1978).
20. A. F. Fercher. In vivo measurement of fundus pulsations by laser interferometry. *IEEE J Quan Electronics.* QE-20, 1469-1471 (1984).
21. R. W. Flower. Extraction of choriocapillaris hemodynamic data from ICG fluorescence angiograms. *Invest Ophthalmol. Vis Sci.* 34, 2720-2729 (1993).
22. Y. Hirata, H. Nishiwaki, S. Miura, et al. Analysis of Choriocapillaris flow patterns by continuous laser targeted angiography in monkeys *Invest. Ophthalmol Vis Sci,* 45, 1954-1962 (2004).
23. C. Riva, B. Ross, G. B. Benedek. Laser Doppler measurements of blood flow in capillary tubes and retinal arteries. *Invest Ophthalmol* 11, 936-944 (1972).
24. M. D. Stern, D. L. Lappe, P. D. Bowen, et al. Continuous measurement of tissue blood flow by laser Doppler spectroscopy. *Amer J Physiol.* 232, H441-H448 (1977).
25. C. P. J. Cuypers, H. S. Chung, L. Kagemann, Y. Ishii, D. Zarfati, A. Harris. New neuroretinal rim blood flow evaluation method combining Heidelberg retina flowmetry and tomography. *Br J Ophthalmol* 85, 304-309 (2001).
26. A. Harris, P. C. Jonescu-Cuypers, L. Kagemann, A. T. Ciulla, K. G. Krieglstein, Atlas of ocular blood flow-vascular anatomy, pathophysiology, and Metabolism, Philadelphia, Pa.: Butterworth Heinemann; 54-61 (2003).
27. C. W. C. Klaver, C. W. R. Wolfs, R. J. Vingerling, T. V. P. de Jong, Age-specific prevalence and causes of blindness and visual impairment in an older population, Arch Ophthalmology, 116, 653-658 (2007).
28. J. J. Wang, R. Klein, W. Smith, E. K. B. Klein, S. Tomany, P. Mitchell, Cataract surgery and the 5-year incidence of late-stage ange-related maculopathy, Ophthalmology, 110, 1960-1967 (2003).
29. K. S. West, R. Klein, J. Rodriguez, B. Munoz, T. A. Broman, R. Sanchez, R. Snyder, Diabetes and diabetic retinopathy in a Mexican-American population, Diabetes Care, 24, 1204-1209 (2001).
30. J. Flammer, S. Orgul, V. P. Costa, et al. The impact of ocular blood flow in glaucoma. *Prog Retin. Eye Res.* 21, 359-393 (2002).
31. E. A. Friedman, Hemodynamic model of the pathogenesis of age-related macular degeneration. *Am J Ophthalmol.* 124, 677-682 (1997).
32. J. Flammer. The vascular concept of glaucoma. *Surv Ophthalmol.* 38, S3-S6 (1994).
33. G. Michelson, M. J. Langhans, M. J. Groh. Perfusion of the juxtapapillary retina and the neuroretinal rime area in primary open angle glaucoma. *J Glaucoma.* 5, 91-98 (1996).
34. J. Kerr, P. Nelson, C. O'Brien. A comparison of ocular blood flow in untreated primary open-angle glaucoma and ocular hypertension. *Am J. Ophthalmol.* 126, 42-51 (1998).

What is claimed is:

1. A method for measuring in vivo blood flow in a predefined region of a subject using Doppler Fourier domain optical coherence tomography (OCT), comprising:
    scanning the region with a scanning pattern comprising at least two different planes to obtain Doppler shiftOCT data, wherein said planes cross blood vessels within said region;
    analyzing the obtained Doppler shift OCT data to determine a vector representing a blood vessel and direction of blood flow in the vessel, wherein said analyzing step comprises comparing data corresponding to two or more planes in the scanning pattern in which the planes cross the same vessel;
    calculating a Doppler angle between the blood vessel and an incident scanning beam incident on the vessel; and
    determining a volumetric blood flow rate using the Doppler shift and the incident angle corresponding to the blood vessel.

2. The method of claim 1, wherein said OCT scanning pattern is one that is capable of crossing all blood vessels entering and leaving the region.

3. The method of claim 1, wherein said OCT scanning pattern crosses said blood vessels at an angle not perpendicular to the blood vessels.

4. The method of claim 1, wherein said scanning pattern is one selected from concentric circles, parallel lines, or arcs.

5. The method of claim 4, wherein said scanning pattern is a double circular scanning pattern.

6. The method of claim 4, wherein said scanning pattern is one that is capable of being completed within a single cardiac cycle.

7. The method of claim 4, wherein said scanning pattern have a distance of less than 300 μm between the scanning planes.

8. The method of claim 1, wherein said volumetric blood flow is the volume of blood flow into or out of the region per unit time averaged over one single cardiac cycle.

9. The method of claim 1, wherein said volumetric blood flow is determined by summing up the volumetric blood flow in the veins.

10. The method of claim 1, further comprising a step of correcting for errors in the OCT scanned data caused by tissue movement.

11. The method of claim 1, further comprising a step of correcting for phase decorrelation.

12. The method of claim 11, wherein said correcting step comprises constructing a standard curve of flow rate versus scanning step size between each axial scan, and correcting the flow rate according to the standard curve.

13. The method of claim 1, wherein said region is the optic disc of a subject's eye.

14. The method of claim 1, wherein said subject is human.

15. The method of claim 1, wherein said determining step comprises at least one of the following: obtaining a 2D speed distribution corresponding to the cross-section of the blood vessels, calculating a pulsation factor, or calculating an angle between the plane of the vessel's cross-section and the normal of the vessel.

16. The method of claim 1, wherein said method is computer implemented.

17. A method of diagnosing a disease condition related to blood flow, comprising:
monitoring blood flow at a location indicative of the diseased condition using the method of claim 1.

18. The method of claim 17, wherein said diseased condition is one selected from glaucoma or vein occlusion.

19. The method of claim 17, wherein said location is the optic disc of the eye.

20. A method for determining a local blood flow rate in a subject by Doppler Fourier domain optical coherence tomography, comprising:
obtaining at least one pair of Doppler scan images containing Doppler shift signals, wherein each of the images in the pair correspond to a plane in a pair of planes intersecting at least one blood vessel;
defining a vector corresponding to the direction of the scanning beam and a vector corresponding to the direction of blood flow using coordinates of the blood vessels in the images;
calculating an incident angle between the scanning beam and the blood vessels using the vector of the scanning beam and the vectors of the blood vessels; and
determining the blood flow rate using the Doppler shift signals in the blood vessels and the corresponding incident angle.

21. The method of claim 20, wherein said planes intersect a portion of the subject's body to define a scanning pattern selected from circulars, lines, or arcs.

22. The method of claim 21, wherein said Doppler scans have a frame rate of at least 4 Hz.

23. The method of claim 20, wherein said planes circumscribe a location of interest in the subject.

24. The method of claim 23, wherein said location is the optic disc of the subject's eye.

25. The method of claim 23, wherein volumetric flow is determined by calculating the blood flow leaving the circumscribed location.

26. The method of claim 20, further comprising a step of correcting phase decorrelation.

27. A system for measuring and monitoring local blood flow, comprising:
spectrometer based Doppler Fourier domain optical coherence tomography instrument; and
a processing unit operatively connected to the instrument, wherein said processing unit is configured to perform the method of claim 20.

28. A non-transitory computer readable medium having encoded thereon instructions for performing the method of claim 20.

29. A method of measuring total retinal blood flow rate in a subject using Doppler Fourier domain optical coherence tomography, comprising:
scanning the optical disc of the subject in a circular pattern to obtain Doppler images, wherein said circular pattern comprises two or more concentric circles circumscribing the entire optical disc such that the scanned images represent two parallel planes intersecting the optical disc;
analyzing the Doppler images to identify all the veins leaving the optical disc and their respective Doppler angles; and
determining a volumetric flow rate for each vein and summing the volumetric flow rate to arrive at the total retinal blood flow rate.

30. The method of claim 29, further comprising a step of correcting for scanning density phase decorrelation effect.

* * * * *

UNITED STATES PATENT AND TRADEMARK OFFICE
CERTIFICATE OF CORRECTION

| | | |
|---|---|---|
| PATENT NO. | : 8,244,334 B2 | Page 1 of 1 |
| APPLICATION NO. | : 12/101006 | |
| DATED | : August 14, 2012 | |
| INVENTOR(S) | : David Huang and Yimin Wang | |

It is certified that error appears in the above-identified patent and that said Letters Patent is hereby corrected as shown below:

In the Specification

Column 1, Lines 26-29:
Please amend this section as follows:
This invention was made with government support under EY003040 and EY013516, awarded by the National Institutes of Health. The government has certain rights in the invention.

Signed and Sealed this
Fifth Day of March, 2024

Katherine Kelly Vidal
Director of the United States Patent and Trademark Office